(12) United States Patent
Rahbar-Dehghan

(10) Patent No.: US 6,587,197 B1
(45) Date of Patent: Jul. 1, 2003

(54) MULTIPLE MICROCHANNELS CHIP FOR BIOMOLECULE IMAGING, AND METHOD OF USE THEREOF

(75) Inventor: Fariborz Rahbar-Dehghan, Westmount (CA)

(73) Assignee: Royce Technologies LLC, Las Vegas, NV (US)

(*) Notice: Subject to any disclaimer, the term of this patent is extended or adjusted under 35 U.S.C. 154(b) by 348 days.

(21) Appl. No.: 09/634,709

(22) Filed: Aug. 7, 2000

Related U.S. Application Data
(60) Provisional application No. 60/168,767, filed on Dec. 6, 1999.

(51) Int. Cl.[7] .......................... G01N 21/64; G01N 21/01
(52) U.S. Cl. ..................... 356/318; 356/246; 250/458.1
(58) Field of Search ............................. 356/318, 440, 356/246; 250/458.1, 459.1, 461.1, 461.2; 422/82.07, 82.08, 102, 942; 435/288.4, 288.7; 436/172

(56) References Cited

U.S. PATENT DOCUMENTS

| | | | |
|---|---|---|---|
| 2,956,931 A | 10/1960 | Goldberg | |
| 3,107,204 A | 10/1963 | Brown et al. | |
| 4,039,247 A | 8/1977 | Lawman et al. | |
| 4,088,448 A | 5/1978 | Lilja et al. | |
| 4,154,795 A | 5/1979 | Thorne | |
| 4,319,841 A | 3/1982 | Suovaniemi et al. | |
| 4,447,546 A | 5/1984 | Hirschfeld | |
| 4,480,031 A | 10/1984 | Shaw | |
| 4,483,925 A | 11/1984 | Noack | |
| 4,493,815 A | 1/1985 | Fernwood et al. | |
| 4,599,315 A | 7/1986 | Terasaki et al. | |
| 4,673,651 A | 6/1987 | Rothenberg et al. | |
| 4,722,598 A | 2/1988 | Ford | |
| 4,761,378 A | 8/1988 | Godsey | |
| 4,981,345 A | 1/1991 | Berry et al. | |
| 5,002,889 A | 3/1991 | Klein | |
| 5,096,676 A | 3/1992 | McPherson et al. | |
| 5,110,556 A | 5/1992 | Lyman et al. | |
| RE34,133 E | 11/1992 | Thorne | |
| 5,200,152 A | 4/1993 | Brown | |
| 5,219,528 A | 6/1993 | Clark | |
| 5,290,705 A | 3/1994 | Davis | |
| 5,308,584 A | 5/1994 | Vauramo | |
| 5,424,213 A | 6/1995 | Mougin | |
| 5,457,527 A | 10/1995 | Manns et al. | |
| 5,608,517 A | 3/1997 | Munk | |
| 5,700,655 A | 12/1997 | Croteau et al. | |
| 5,738,825 A | 4/1998 | Rudigier et al. | |
| 5,840,256 A | 11/1998 | Demers et al. | |
| 5,843,767 A | 12/1998 | Beattie | |
| 6,022,700 A | 2/2000 | Monks et al. | |
| 6,037,168 A | 3/2000 | Brown | |
| 6,074,614 A | 6/2000 | Hafeman et al. | |

FOREIGN PATENT DOCUMENTS

EP 0233 385 12/1986

OTHER PUBLICATIONS

Mark Schens, PhD, Microarray Biochip Technology, Chapter 5—The Flow-Thru Chip: A Three Dimensional Biochip Platform, Apr. 2000.

Primary Examiner—F. L. Evans
(74) Attorney, Agent, or Firm—Hogan & Hartson, LLP

(57) ABSTRACT

A panel chip for supporting biological samples for observation with a microscope. The glass panel defines a top flat surface, a bottom bearing surface, and at least a few channels extending generally parallel to each other from top to bottom surfaces. Each of the channels defines a top access mouth for ingress of biological samples, wherein each channel is obliquely inclined so as to make a significant acute angle relative to an axis perpendicular to said top flat surface, in order to facilitate the guidance of maximum light into the channel due to zero loss of reflection and to produce the maximum number of total internal reflection and to guide the maximum light out of the microchannel in such a manner that produces no artifact halo for maximum detection and sensitivity. Each channel has such an inner diameter as to accommodate flow through viscosity of a biological sample containing fluid.

20 Claims, 9 Drawing Sheets

MULTIPLE MICROCHANNELS CHIP FOR BIOMOLECULE IMAGING, AND METHOD OF USE THEREOF

CROSS REFERENCE DATA

This application claims convention priority based upon provisional application No. 60/168,767 dated Dec. 6, 1999.

FIELD OF THE INVENTION

This invention relates to providing a microchannel chip device which will be able to perform a large number of bio molecule tests simultaneously, as well as producing a uniform test environment for each biomolecule test and eliminate the statistical test to test variations.

BACKGROUND INVENTION

It is known in fluid dynamics that, due to the viscosity of the biological sample containing fluid, which is usual water, the dynamic pressure to pass this fluid through and into the multiple channel glass panel increases as the microchannel diameter is reduced and the glass plate thickness increases. Threshold values are such that, below 10 micrometers in channel diameter, increase in vacuum pressure is required to force water through the microchannels, and also structural integrity of the glass sample then becomes problematic. However, on the other side, by increasing channel diameter beyond 10 microns and reducing the thickness of the glass plate, vacuum pressure is still required but to a lesser extent, while undesirable artifacts are generated in particular increased diffuse halos around the top access mouth of the channels. These undesirable artifact halos considerably deteriorate both the image quality and the sensitivity of the test.

It is noted that fluid dynamics in a microchannel are not the same as those in diametrally larger tubes, e.g. a water filled coffee mug. Indeed, because of the larger inner diameter of a coffee mug, when a water filled coffee mug is tilted from an upright condition to a laterally inclined position, the top surface menisk of the volume of water will not concurrently tilt and thus will remain parallel to the ground in both instances, although the longitudinal axis of the mug is no longer vertical in its tilted condition. On the other end, due to surface tension properties and viscosity of the water and due to the micrometer grade diameter of the microscopic (micro-) channel, when a microchannel is tilted from an upright condition to a laterally inclined condition, the menisk will not stay parallel to the ground as it did in larger diameter cylinder such as a coffee mug, and it will tilt. With the tilted microchannel so that the perpendicular axis to the top surface menisk of the water volume inside the tilted microchannel will remain coaxial to the longitudinal axis of the tilted microchannel.

U.S. Pat. No. 5,843,767 issued on Dec. $1^{st}$ 1998 to HOUSTON ADVANCED RESEARCH CENTER (inventor: Kenneth BEATTIE)—hereinafter the "Beattie patent", discloses a device for binding a target molecule, comprising a substrate having a multiplicity of discrete tubes extending transversely therethrough. These tubes extend orthogonally to the top surface of the substrate. A first binding reagent is immobilized on the walls of a first group of tubes, while a second binding reagent is immobilized on the walls of a second group of the tubes. Such device is for use in the identification or characterization of nucleic acid sequences through nucleic acid probe hybridization with samples containing an uncharacterized polynucleic acid, e.g. recombinant DNA, polymerase chain reaction fragments, etc . . . as well as other biomolecules.

In the Beattie patent, these tubes are claims limited to a diameter ranging between about 0.03 to 10 micrometers. The reason for the top threshold diameter value is that if your have upright tubes or channels as in Beattie, any diameter larger than about 10 micrometers will enlarge optical halo artifacts at the top access mouth of the tubes, and accordingly, much reduced sensitivity.

During the 1990s, microfabrication technology has enables miniaturization and automation of manufacturing processes in numerous industries. The impact of microfabrication technology in biomedical research can be seen in the growing presence of microprocessor controlled analytical instrumentation and robotics in the laboratory engaged in high throughput genome mapping and sequencing (see the current "Human Genome Project", with its first phase just completed). Optical detection of fluorescent labelled receptors is employed inter alia in detection for sequencing. Detection can be achieved through use of a charge coupled device array, or confocal laser imaging technology such as DNA scope (TM).

Capillary tube glass arrays are already in use as high surface area nanoporous support structures to tether DNA targets or probes for hybridization. Such capillary tube glass wafers contain a regular geometric array of parallel holes or tubes as small as 33 nanometers in diameter, or as large as several micrometers in diameter. These holes or tubes serve as sample wells for placement of a substantially homogeneous sample of a biomolecule within each hybridization site. The orifices are fabricated using excimer laser machining.

However, such prior art microscopic detection devices usually require charged coupling devices, and cannot scan the full sample area. This is because, as in the Beattie patent, since you have vertical micro-channels, the diameter thereof larger than 10 micrometers will produce much larger optical halo artifacts and will bring about much diminished microscopic sensitivity. This is why the claimed microchannel diameter in the Beattie patent is limited to a range from 0.03 to 10 micrometers.

Methods are also known in the art for delivering subnanoliter microdroplets of fluids to a surface at submicron precision. A microjet system or a microspotter, capable of delivering subnanoliter DNA solution to the wafer surface, can thus be employed.

OBJECTS OF THE INVENTION

An important object of the present invention is therefore to improve upon the above-noted prior art technology, in particular to that disclosed in the Beattie patent, supra, by providing a device which will be able to perform a large number of bio molecule tests simultaneously, as well as producing a uniform test environment for each biomolecule test and eliminate the statistical test to test variations.

A further important object of the present invention is to use the capillary tube as an environment that can produce an internal reflection known as "pipping effect", so as to increase sensitivity and resolution of biomolecule detection.

Still another object of the invention is to use the capillary tube as an environment in which samples and reagents flow through, to increase the interactions between biomolecules so as to reduce the incubation time and increase the sensitivity and resolution at the same time, to thus enable use of a more diluted sample for the same efficiency.

A general object of the invention is to reduce labour costs and required effective sample volume associated with operation of such devices.

SUMMARY OF THE INVENTION

According to the invention, there is disclosed a rigid panel chip for supporting biological samples for observation with a microscope, said glass panel defining a top flat surface, a bottom bearing surface, and at least a few channels extending generally parallel to each other from said top to bottom surfaces, each of said channels defining a top access mouth for ingress of said biological samples, wherein each of said channel is obliquely inclined so as to make an acute angle relative to an axis perpendicular to said top flat surface, and each said channel having such an inner diameter as to accommodate flow through viscosity of a biological sample containing fluid.

Preferably, the panel chip consists of either glass, quartz, polypropylene, polyolefin, nylon, or fused silica. More preferably, the panel chip will be made from transparent glass. Most preferably, the glass chip will have a thickness ranging between 0.5 to 5 millimeters.

Preferably, said channels are cylindroid. Preferably, said cylindroid channels have a constant diameter ranging between 10 to 500 micrometers, more preferably, between 50 to 200 micrometers, and most preferably, of about 100 micrometers.

Said acute angle should range between 20 to 80 degrees, and preferably be about 42 degrees.

Preferably, the number of said channels range between a few hundreds to a few thousands of said channels extending through the thickness of said glass panel.

The invention also relates to a method of observation by flat surface laser scanner of biological samples in a glass panel, the glass panel of the type defining a top flat surface, a bottom bearing surface, and a plurality of channels extending generally parallel to each other from said top to bottom surfaces and each defining a top access mouth for the biological sample, the method including the following steps:

a) inclining the channels in an oblique fashion so as to make an acute angle relative to an axis perpendicular to the top flat surface of the glass panel, b) enlarging the inner diameter of each said channel enough as to accommodate reduced vacuum assisted flow through viscosity of a biological sample containing fluid;

c) providing fluorescein dyes inside the biological sample containing fluid;

d) directing a coherent laser beam transversely through a selected channel top access mouth and coaxially into the corresponding channel, so as to excite the fluorescein dyes, wherein an optically apparent glow is generated by the excited fluorescein dyes without a halo being generated about the top access mouth;

e) allowing sufficient time for the fluorescein dyes to project the optically apparent glow upwardly beyond said channel top access mouth; and f) performing optical measurements of this upward out of channel projecting fluorescein glow by flat surface laser scanner to generate evidence data on the chemical properties of the biological samples.

DETAILED DESCRIPTION OF THE PREFERRED EMBODIMENT OF THE INVENTION.

Figure 1:
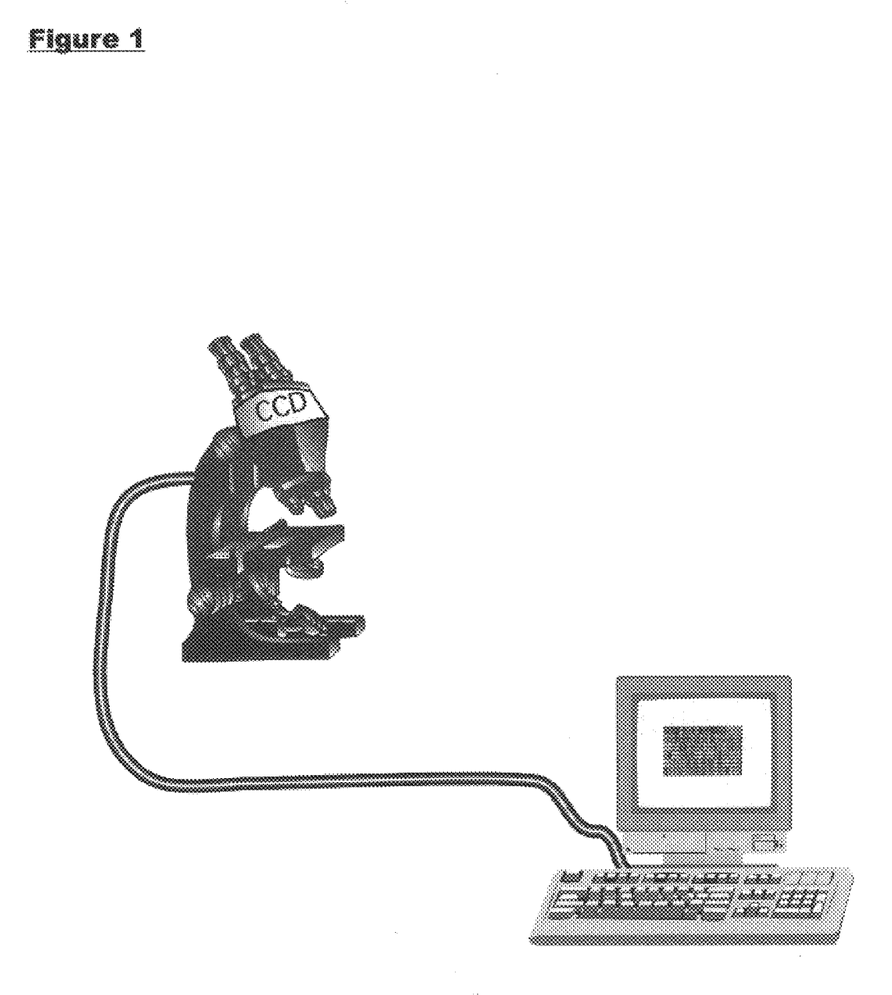
FIG. 1 is a schematic perspective view of a prior art microscope and computer system assembly, coupled to a CCD unit for observing a sample supporting glass plate.
Figure 3:
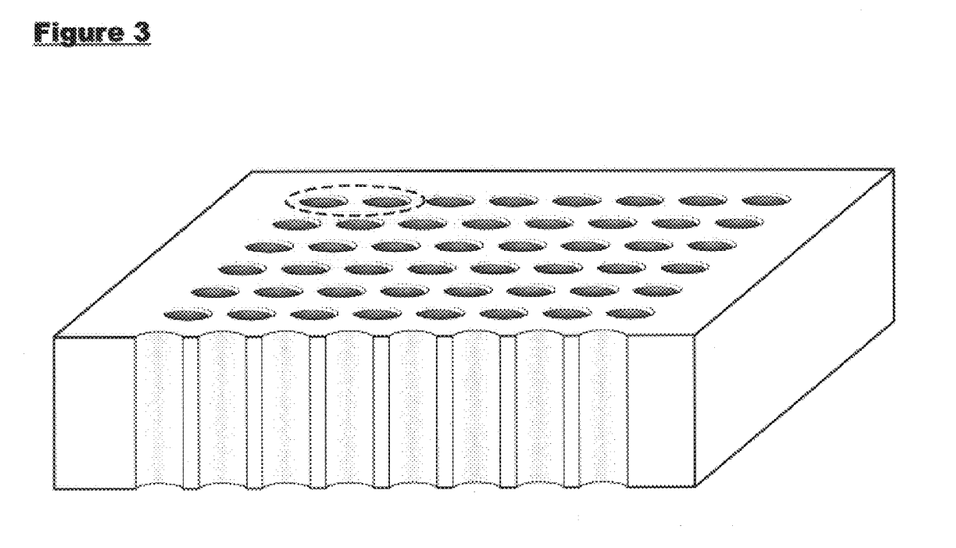
FIG. 3 is an enlarged partly broken isometric and sectional view of a prior art microchip showing that the channels are orthogonal to the chip top surface
Figure 5:
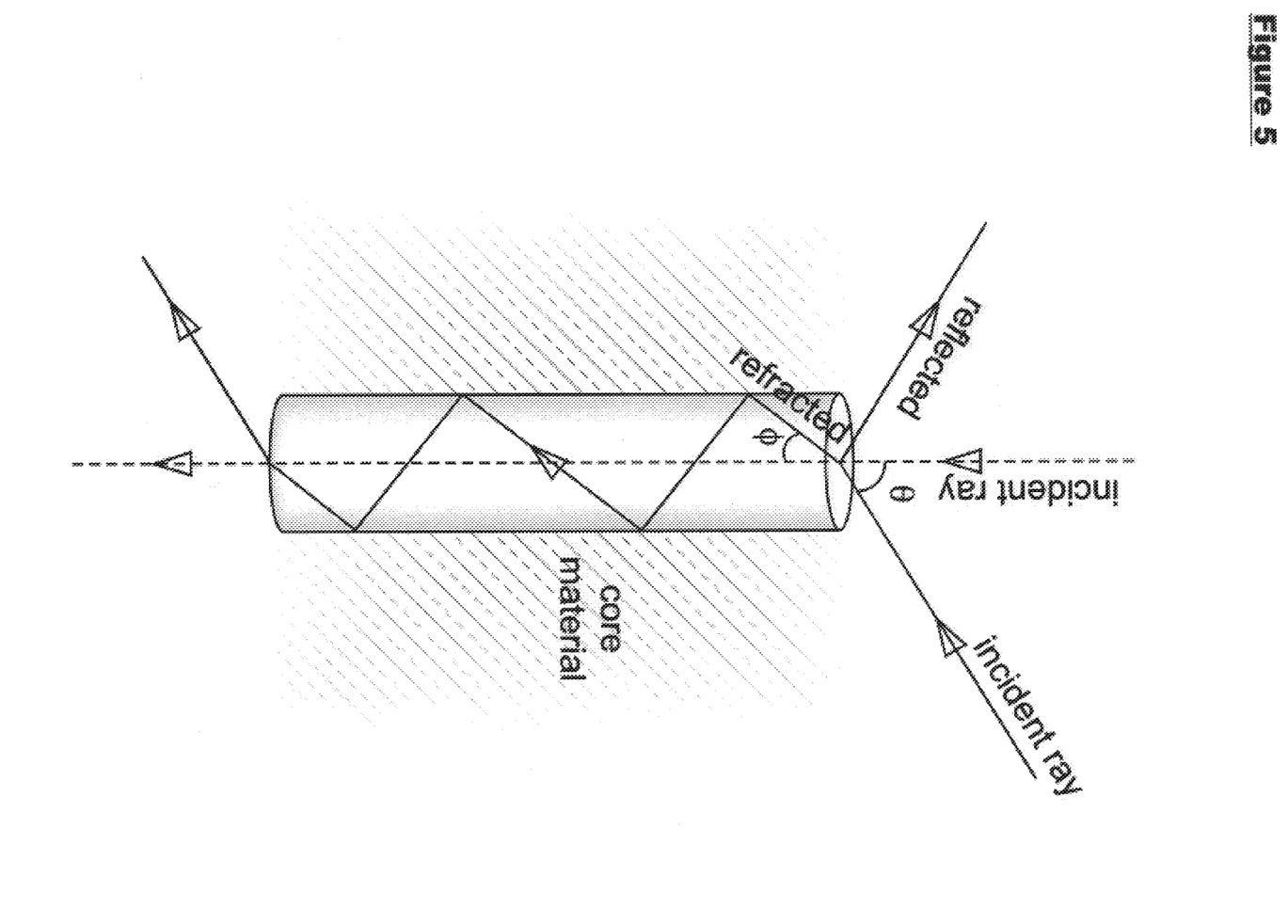
FIG. 5 is a schematic view of a single straight prior art micro-channel similar to those in FIG. 3, showing the light cannot enter the microchannel entirely without losing its power to reflection and also suggesting when the laser beam is directed perpendicular to the surface, it enters the microchannel and exits from the other end without producing total internal reflection.

FIGS. 3 and 5 of the drawings show prior art microchannels such as in the Beattie patent, supra. Each such microchannel is a regularly array of the unilength type in perpendicular position to the surface of the plane. It is vertical or upright, inside the glass observation plate. This microchannel is of uniform length and shape, and is vertical. As further shown in FIG. 1, it needs to be scanned through the entire length of the channel for detection, it requires special scanning device, and is therefore expensive. It has average emission excitation, a cross-talk, and a halo circle around the top sample access end mouth constituting an artifact. It has average to low sensitivity. Its maximum operational diameter is 10 micrometers or less. It further needs seals and vacuum pressure to engage the water sample inside the microchannel, due to the microchannel diameter being too small for unassisted engagement.

Figure 3A:
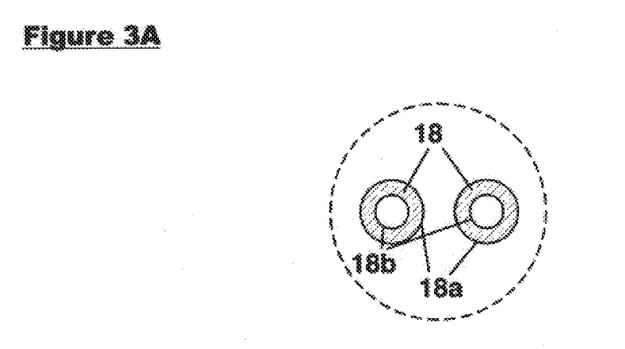
FIG. 3A is a top end view of two adjacent channels from the top chip surface of FIG. 3.

As is shown in prior art FIG. 3A, there is a top end view of two adjacent channels when looking from top through the microchannels. Element 18*a* represents the top opening of the first channel, and element 18*b* represents the bottom opening of the same channels. Element 18 is the inner wall of the microchannels.

When one increases the diameter of the channels from 2 to 200 micrometers, i.e. by two orders of magnitude, the inner surface of the channel will increse by 200 divided by 2, i.e. by 100 times, by the surface area of the black hole. In the prior art system of FIG. 3A, the increase is of 10,000 times, i.e. by four orders of magnitude. This will therefore be a critical factor in deterioration of the image quality which prevents the inner diameter in the channel in FIG. 3A to be operatively more than about 10 micrometers. This is shown in the following calculation in FIG. 3A:

18*b*=2 micrometers (channel diameter) area of inner wall 18 FIG. 3A=2π×H, where H is the height area of opening of each channel: 2/2×2/2×π=π(no unit used)

18*b*=200 micrometers of channel diameter area of inner wall 18 FIG. 3A: 200π×H area of opening of each channel=200/2×200/2×π=10, 000π(no unit used)

We can see that a hundred time set increase in inner wall surface area 18 FIG. 3A, has resulted in 10,000 time (exponential) increase in black hole artifact 18*b* FIG. 3A. But this is not the case in the present invention, as illustrated in FIG. 4A, since there is no black hole or halo artifact represented when the diameter of channels increases from 2 to 200 micrometers. The black hole or halo artifact of the prior art 18*b* FIG. 3A, where there is lack of flurorescent glow, when it is viewed from top position and this gives a dark and halo like appearance in image capturing.

Moreover, inspection of light imaging in prior art FIG. 3A is performed through tedious multiple scanning of transverse strata along the full length of a chip microchannel, contrary to the surface scan of the present invention at FIG. 4A.

Figure 2:
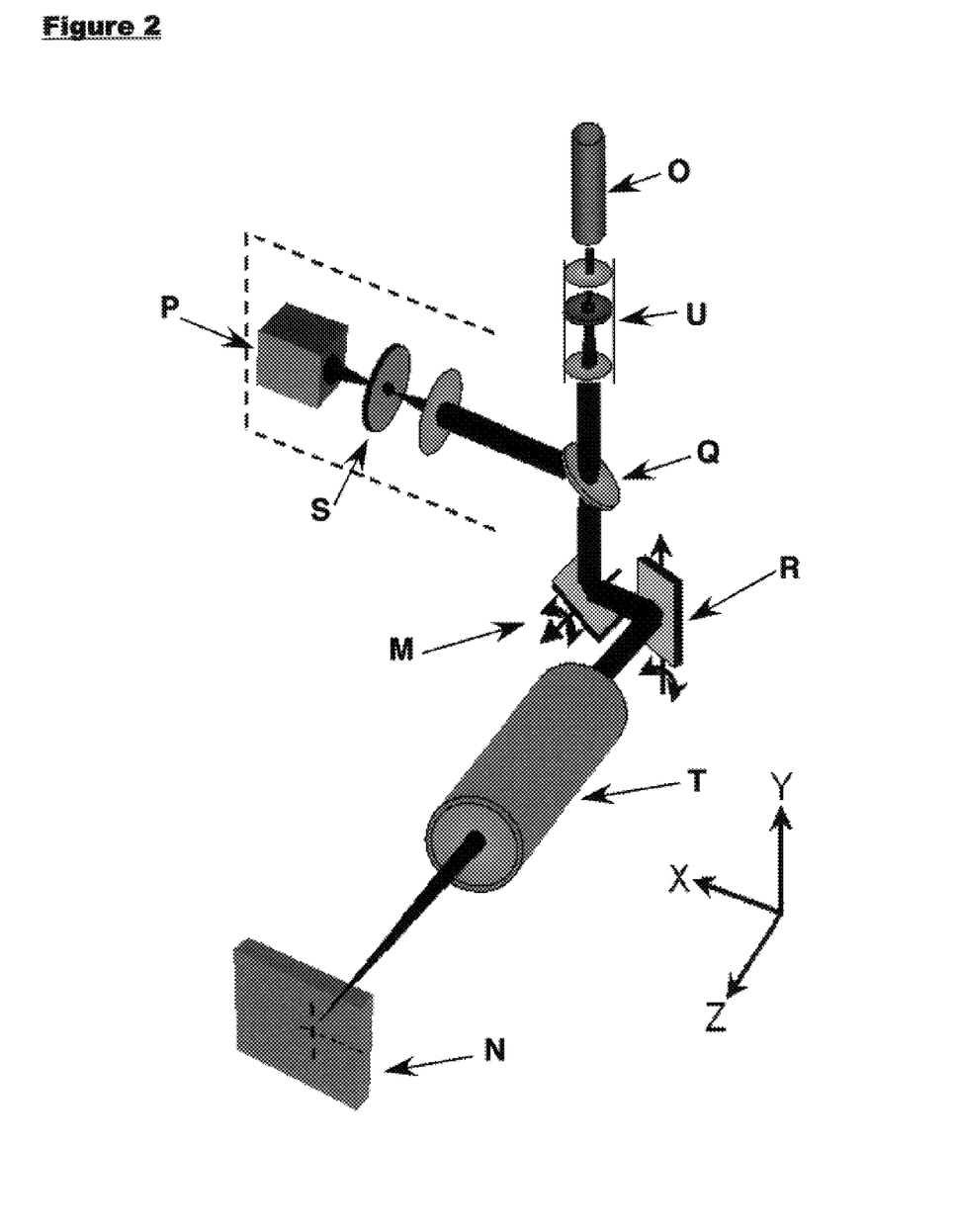
FIG. 2 is a schematic perspective view of a confocal imaging system for surface inspection on a specimen holder of a microchip according to the present invention.

FIG. 2 alternately shows a confocal imaging system for use with the chip of the present invention. System M includes a specimen holder N, for supporting the sample containing chip, a laser gun O for beaming light onto the specimen holder, and a black hole light detector P, for imaging the biomolecules inside the chip channels. A beam splitter Q and tilted mirror assembly R, is mounted intermediately of the specimen holder, light detector and laser gun. A pinhole member S is mounted between the light detector and beamsplitter. A laser scan lens T is mounted between the specimen holder and the scanning mirrors. A spatial filter and beam expander, U, is mounted between the laser gun and the beamsplitter.

In FIG. 2, the beamsplitter allows both free laser beam passage from gun O to specimen holder N in a first direction, and return passage of the biomolecule imaging beam from the specimen holder to the detector P through reflection against intermediate beam splitter Q. The light detector should be coupled to a suitable microscope, for example a microscope having parfocal arms and submicron diffraction limited resolution with 12 or 16 bit dynamic range detection, such as for example sold under the MACROSCOPE or DNAscope trademarks by BIOMEDICAL, PHOTOMETRICS inc. (Waterloo, Canada).

Figure 6:
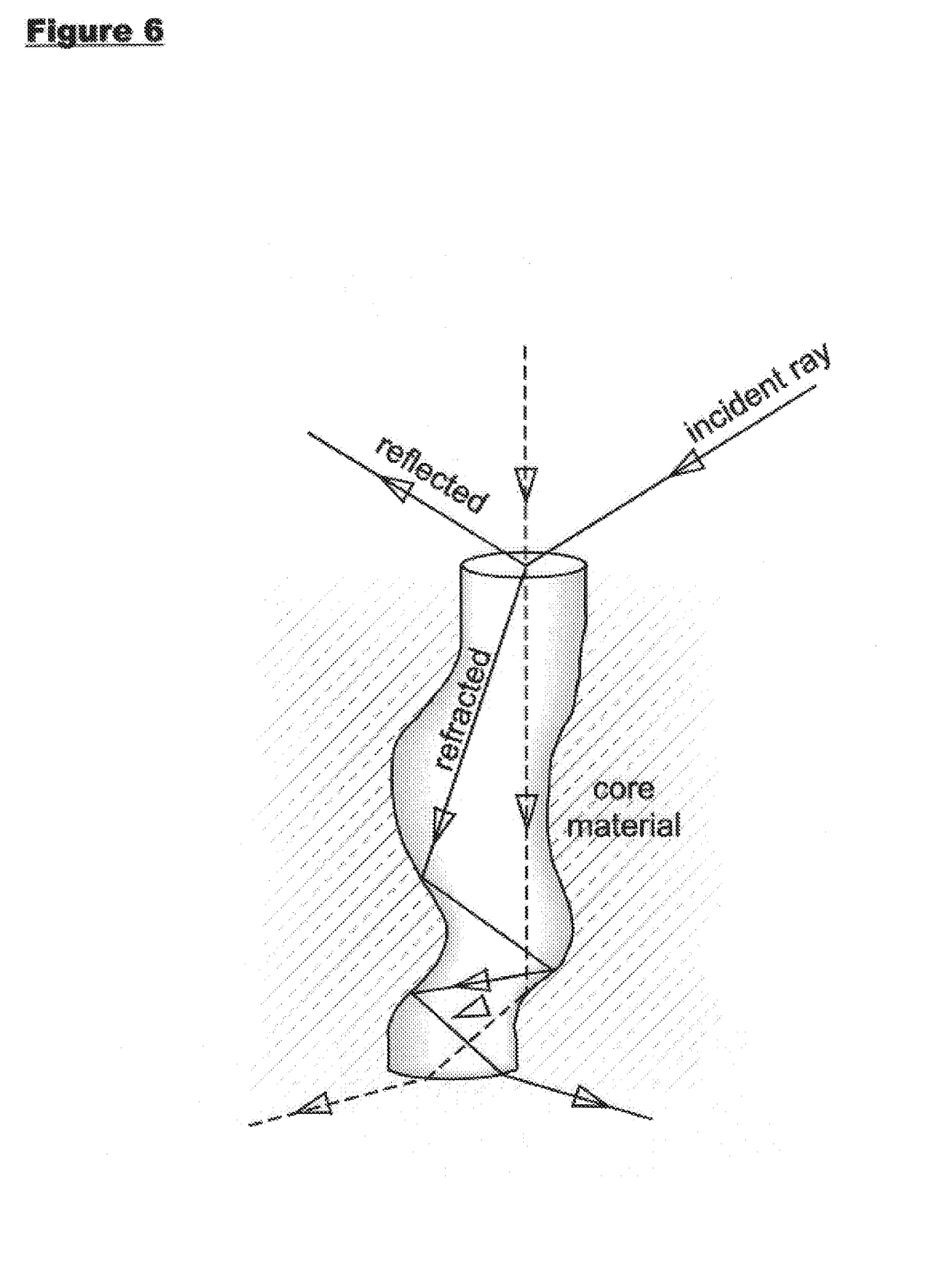
FIG. 6 is a schematic view of another isolated prior art irregularly shaped microchannel, suggesting how light can not enter entirely into the channel without having some being reflected, this nanoporous silicon with non uniform inner wall showing scattered internal reflection which contributes to an increase in cross-talk and light escaping from the micro-channels.

FIG. 6 of the drawings shows an alternate prior art microchannel. This porous silicon nanochannel, which has a diameter of less than 1 micron, i.e. about 0.03 micron, is an irregularly shaped array of variable length and size. It is of non uniform size and length. Its level of excitation emission is minimal. It has maximum cross-talk. Again, it has a small inner diameter of less than 1 micrometer, meaning once again that for engagement of sample fluid therein, high vacuum pressure is required, which results in compromising the structural integrity of the chip. Also, various sample fluid quantity is bounded due to varying length and non uniformity.

Figure 4:
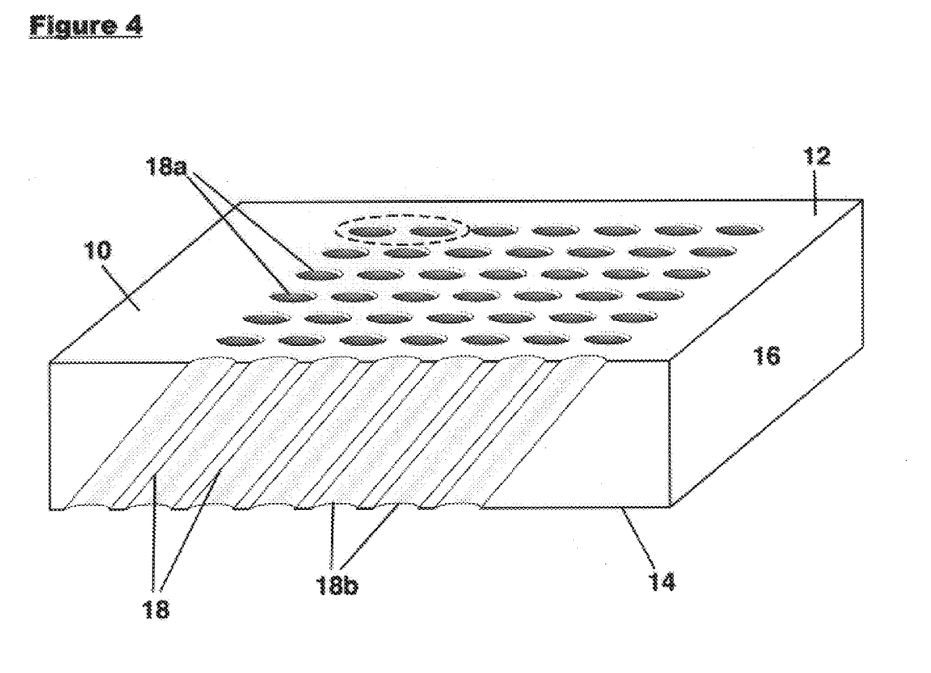
FIG. 4 is an enlarged partly broken isometric and sectional view of the multiple channel glass plate of the invention, showing the slant of the oblique channels made through the thickness of the glass plate chip.
Figure 4A:
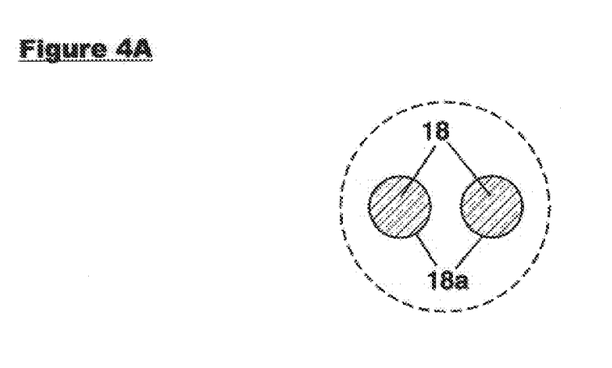
FIG. 4A is a view similar to FIG. 3A but for the present invention chip, and suggests that the observer has no direct line of sight between the top and bottom ends of each through micro-channel.
Figure 7:
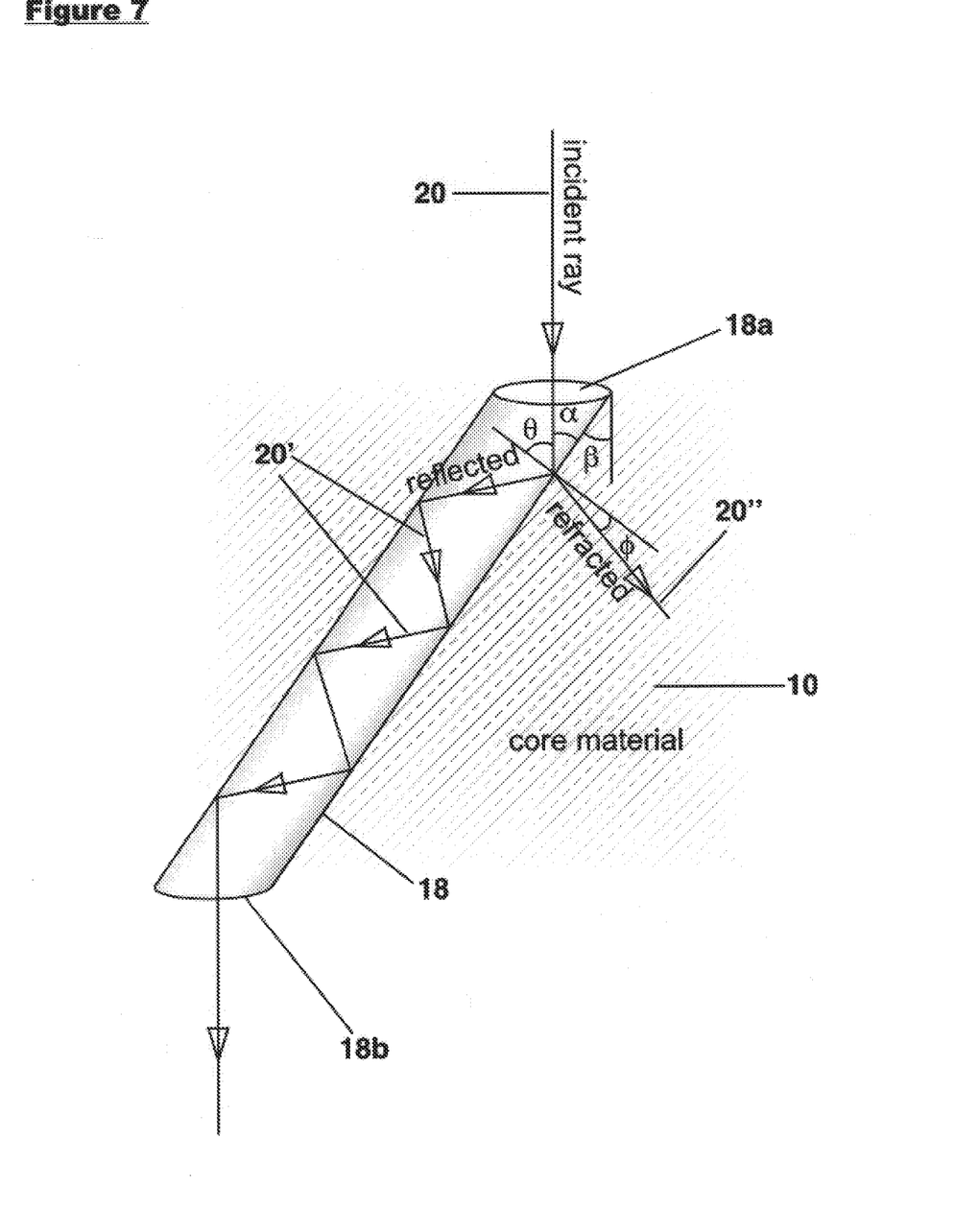
FIG. 7 is a view similar to FIGS. 5 and 6, but showing the preferred embodiment of slanted channel inside the glass panel chip according to the present invention.

FIGS. 4 and 7 show a micro-channel 10 according to a preferred embodiment of the present invention. The glass plate 10 defines top and bottom flat surfaces 12, 14, respectively, being parallel to one another, spaced by a full thickness glass body 16. The present invention microchannel forms a regular array of uniform length microchannel tubes and extends along a pre-established constant angular orientation. More particularly, the hollow microchannel 18 extends obliquely relative to an axis perpendicular to both top and bottom flat surfaces 12 and 14. The bottom flat surface 14 is the bearing surface of the glass plate. The top mouth 18*a* of the microchannel 18 is coplanar to the top flat surface 12 of the glass plate, while the bottom mouth 18*b* of the microchannel 18 opens at the bottom flat surface 14 of the glass plate. The microchannel is of uniform throughout length, and provides an oblique fluid flow through. This microchannel can use CCD (charged coupling device), PMT (photomultiplier tube) or flat surface laser scanners, for biological sample detection. It has maximum emission excitation. It has minimum cross-talk. Most importantly, no artifact halo circle is generated at the top mouth 18*a*, where observations are performed preferably by a flat surface laser scanner. The present invention microchannel has maximal internal reflection and maximal sensitivity features. It is a larger microchannel diameter than the prior art ones, bringing about less plumbing problems. Since detectors P are placed on top of channels, the light which exits the channels are in vertical column and parallel to each other without having the blackhole in the center.

In the present invention microchannel, the obliqueness thereof relative to the glass panel top surface, forms a fixed angular value being computed from snell's law:

n1 sin θ=n2 sin φ with the refractive index of air being by definition 1, of water, 1.33, and of glass, ranging between 1.41 to 1.61 (with an average of 1.51) depending on the manufacturer.

As is known from college level physics, Snell's law is a law of geometric optics, that defines the amount of bending that takes place when a light ray strikes a refractive boundary. Where n1 is the index of refraction of the medium in which the incident ray travels, θ is the angle with respect to the normal at the refractive boundary at which the incident ray strikes the boundary, n2 is the index of refraction of the medium in which the refracted ray travels, and φ is the angle with respect to the normal at the refractive boundary at which the refracted ray travels. If a ray travels from a medium of lower refractive index into a medium of higher refractive index, it is bent toward the normal. If it travels from a medium of higher refractive index to a medium of lower index, it is bent away from the normal. Total internal reflection occurs when light, in a higher refractive index medium, strikes an interface with a medium with a lower refractive index, at an angle of incidence (with respect to the normal) greater than the critical angle. This reflection occurs even in the absence of a metallic reflective coating (e.g. aluminum or silver).

This microchannel obliqueness critically enables the laser light beam to penetrate the sample containing fluid inside the microchannel at its maximum strength.

For calculating the oblique angle β of the microchannel, i.e. the angle between the longitudinal axis of the microchannel and the axis perpendicular to the top surface of the glass panel into the thickness of which the microchannel is nested, this is based on the properties of the glass material and the refractive index:

$$\alpha+\beta=90°$$

$$\beta+\theta=90°$$

$$\beta=90-\theta$$

The incident ray of the laser beam is perpendicular to the top surface of the sample glass plate, so the laser beam penetrates to the maximum without any undesirable reflection; that is important since the stronger the beam, the more fluorescein dyes within the channel will be excited.

As suggested in FIG. 7 of the drawings on file, once the laser beam 20 hits the glass side wall of the channel tube, it produces both reflected beams 20' and refracted beams 20". If angle θ has a value of 90 degrees, it is parallel to the side of the glass core, and remains inside the channel tube. If on the other hand angle θ has a value of zero, then the light will exit the channel tube. The critical angle is chosen where the maximum internal reflection to occur and minimum light to escape from the tube 18. This critical angle is important because if the angle is less than this value, some light goes through the chip glass core and escapes from the light channel tube 18. Let's assume that the critical angle for a glass material with refractive index of 1.46 is equal to 44°. The oblique angle β=α=90−44=46. This oblique angle is set to produce the maximum total internal reflection and the minimum loss due to refracted beam.

Alternately, the chip could be made from non-transparent material. Then, the microchannel 18' should be lined with an inner light reflecting coating 18a', preferably made from a metallic material selected from the group comprising aluminum and silver. In this format, this alternate embodiment of chip 10' need not be transparent. The channels still remain in oblique flow shape but there is a reflective metallic coating 18a' (see FIG. 8). This metallic coating will usually be aluminum, having an average of 90% reflectivity between 200 and 1000 nanometers (nm). Also, vacuum deposited of several other metals makes excellent reflectors. The protective monolayer 22 in FIG. 8, shields layer 18a' from oxydation that can be a deposit of silicon (SiO2) or magnesium fluoride (MgF2) or the other, to insure high reflectance from the UV to the infrared range. The oblique flow shape of the micro-channels help to ensure that the maximum level of light penetrates and exits from the microchannels. Since the inner channels are coated with reflective material, the light does not escape to the core material and exit at its maximum. Therefore, there is no Snell's law or critical angle, but only an oblique angle.

We will now address the present invention oblique flow technology. Although flow through chip known as the three dimensional chip has many advantages over the flat surface chip, there are nevertheless major inherited problems with the nature of these chips that make them highly undesirable and economically unattractive. These problems include:

plumbing;

detection; and use of expensive microscopy and devices that can scan the length of the channel, for detection.

On the other hand, with oblique flow technology, there is a new class of three-dimensional gene chip that has addressed these problems.

With the plumbing problem, the pressure required to pass liquid through the top access mouth of the microchannel, increases as the microchannel diameter is reduced and the glass plate thickness is increased. More particularly, as the prior art microchannel inner diameter decreases below 10 μ (micrometers), there is required a higher vacuum pressure level and it becomes problematic in maintaining structural integrity of the chip. On the other hand, by increasing the micro-channel diameter and reducing the glass plate chip thickness, undesirable artifacts are generated including diffuse optical halos around the top access mouth of the microchannel. This halo artifact will deteriorate the image quality of the laser surface scanner, hence the lateral intensity comparison of different micro-channels. Also, by reducing the channel diameter and increasing the number of channels, the structural integrity of the chip will be compromised.

Figure 9:
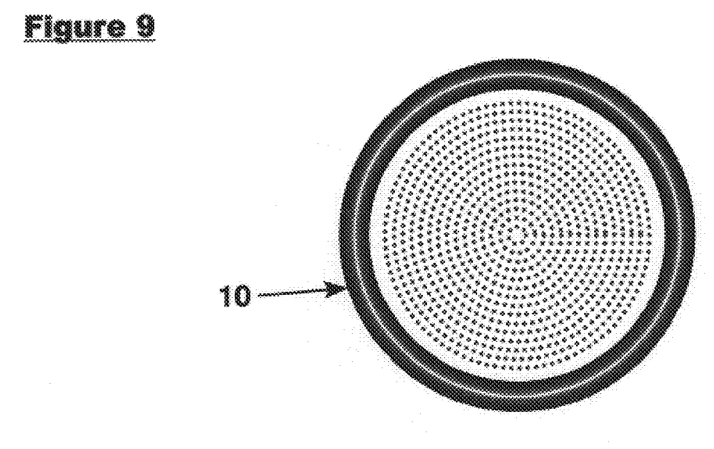
FIG. 9 is a top end view of an alternate embodiment of circular chip of the present invention.
Figure 9A:
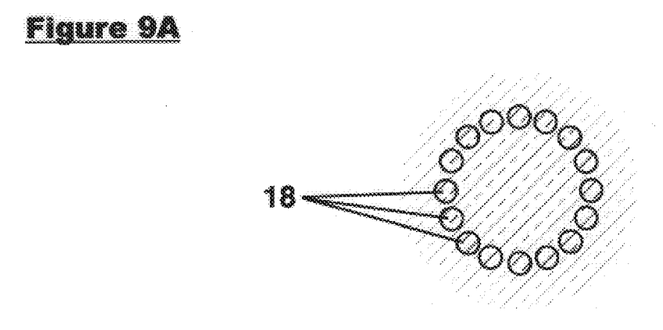
FIG. 9A is an enlarged top end view of a central portion of the circular chip of FIG. 9.
Figure 9B:
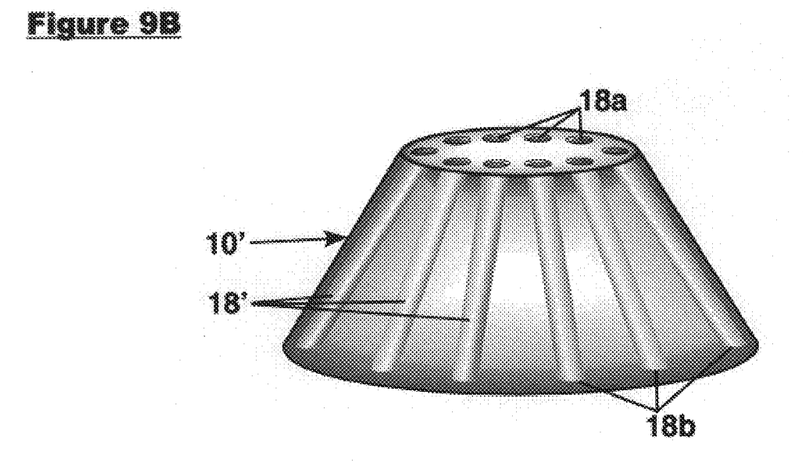
FIG. 9B is an elevational view of still another alternate embodimetn of chip, having a conical shape with the channels disposed in an upwardly radially inwardly inclined peripheral fashion, for use in a centrifuge rather than with a vacuum assist means for the filling and drainage of the biological specimen liquid from the micro-channels.

Alternately, and as illustrated in FIG. 9B, the chip instead of being rectangular (as in FIG. 4), may be conical or circular in shape. The array of micro-channels 18' would then be disposed in an upwardly, radially inwardly inclined fashion. With such an alternate chip 10', the power assist means for drainage and filling of the micro-channels 18' with the biological sample solution, instead of being small vacuum assisted means, can be replaced by a centrifuge. The centrifuge may operate e.g. at 2500 RPM for about 2 minutes, to allow the biological sample solution to engage and settle inside the micro-channels. It is noted that such centrifugal technique for filling the chip oblique microchannels with biological sample solution, would not be effective in the prior art chips having vertical (non-oblique) microchannels. Indeed, in the prior art chips, the liquid inside the microchannels cannot be drained off from the bottom, contrarily to the case with oblique angle micro-channels according to the present invention. The spotting of material on a conical chip is also easier than on a rectangular chip. Imaging detection can be less bulky, since the scanning could be facilitated by the circular motion of circular disk along its center. A hand held and portable device is achieved from afforded size reduction. These are critical differences compared with prior art techniques, generating unexpected results.

As for the detection problem, most prior art microarrays are produced on microscope slide glass, where the binding reaction and signal generation occurs within a single plane. In the three-dimensional layout of gene chip, this binding reaction occurs through the thickness or depth of the chip. Therefore, depth of field becomes more important since the signal must be collected throughout the thickness of the chip. Conventional commercial microarray readers which use confocal scanning optics are not appropriate for these chips. Only expensive custom-built CCDs are large enough to image the entire microarray in a single detection step. Therefore, confocal concept of acquiring signal from a very thin optical slice, enters in conflict with three dimensional geometry of flow through chip. In order to produce a good lateral resolution to distinguish the individual spot, the light should be collected from the entire thickness of the chip. There is therefore a tradeoff in resolution between lateral and depth of field, and this imposes extra weight to the section criteria. The higher the DNA, the greater lateral and depth resolution is achieved. For example, the image area for 1× objective is:

8.5×6.8 mm wherein for 40× objective, it is reduced to;

0.22×0.17 mm.

The present invention oblique flow is much different. Indeed, the oblique flow chip has addressed the above problems with a totally new design. As it is shown in FIG. 7 of the drawings, the light or incident ray must penetrate the microchannel top end mouth and excite the fluorescent molecules present inside the sample fluid, and emission light must be able to escape from within the tube. This is achieved at its maximum efficiency when the incident ray is perpendicular to the top free surface of the chip, and reflected ray is zero. In this scenario, all the light will penetrate the tube. By choosing the θ critical angle for maximum internal reflection and minimum loss of refraction to the chip core material, the oblique angle β can be computed. After the fluorescent molecules from within the channel tubes have been excited, most of the emission light will exit perpendicularly to the top chip surface, which will result in an improved optical collection and detection system, as is shown at 20 in FIG. 7.

In oblique flow:

a) there is no need to collect light from within the entire thickness of the tube, since it can be collected from the top microchannel mouth surface 18*a* surface and act as a flat surface chip. The need for expensive devices with special objective lenses is therefore eliminated.

b) the halo artifact which is seen in conventional three dimensional chip, disappears. This will result in more uniformity and consistency in imaging intensities of various channel when the intensities comparison plays a crucial role in determination of end result. That is to say, as one looks e.g. through an empty tube, the bottom outer end of the tube will obviously disappear from view when the viewer tilts the tube.

c) By increasing the light penetration and emission and maximizing total internal reflection and minimizing the cross-talk, which in turn will increase the detection sensitivity, the channel diameter is allowed to increase, thus enabling decrease of the problem associated with liquid passing through the channels and high pressure vacuum, which jeopardizes the chip structural integrity.

Since the refracted ray is minimized by choosing the right angle θ or critical angle, therefore the cross-talk is minimized.

The cross-talk is an important phenomenon in image analysis. Since most of flat surface chips are scanned using a laser beam, the cross talk could be minimized by directing the incident beam with the appropriate critical angle. This is more noticeable where the light should be travelling through the fiber optics for miles.

On the contrary, in prior art FIG. 6 for example, since the microchannel has non-uniform internal space with different dimension through the lenght of the chips, the cross-talk reaches its maximum and most light will escape from the channels. Moreover, since the length of the microchannels vary and no two channels are the same, there is various quantity of fluorescein dye bounded to these channels; this will in turn result in various intensity due to uneven quantity of bound molecules.

Figure 8:
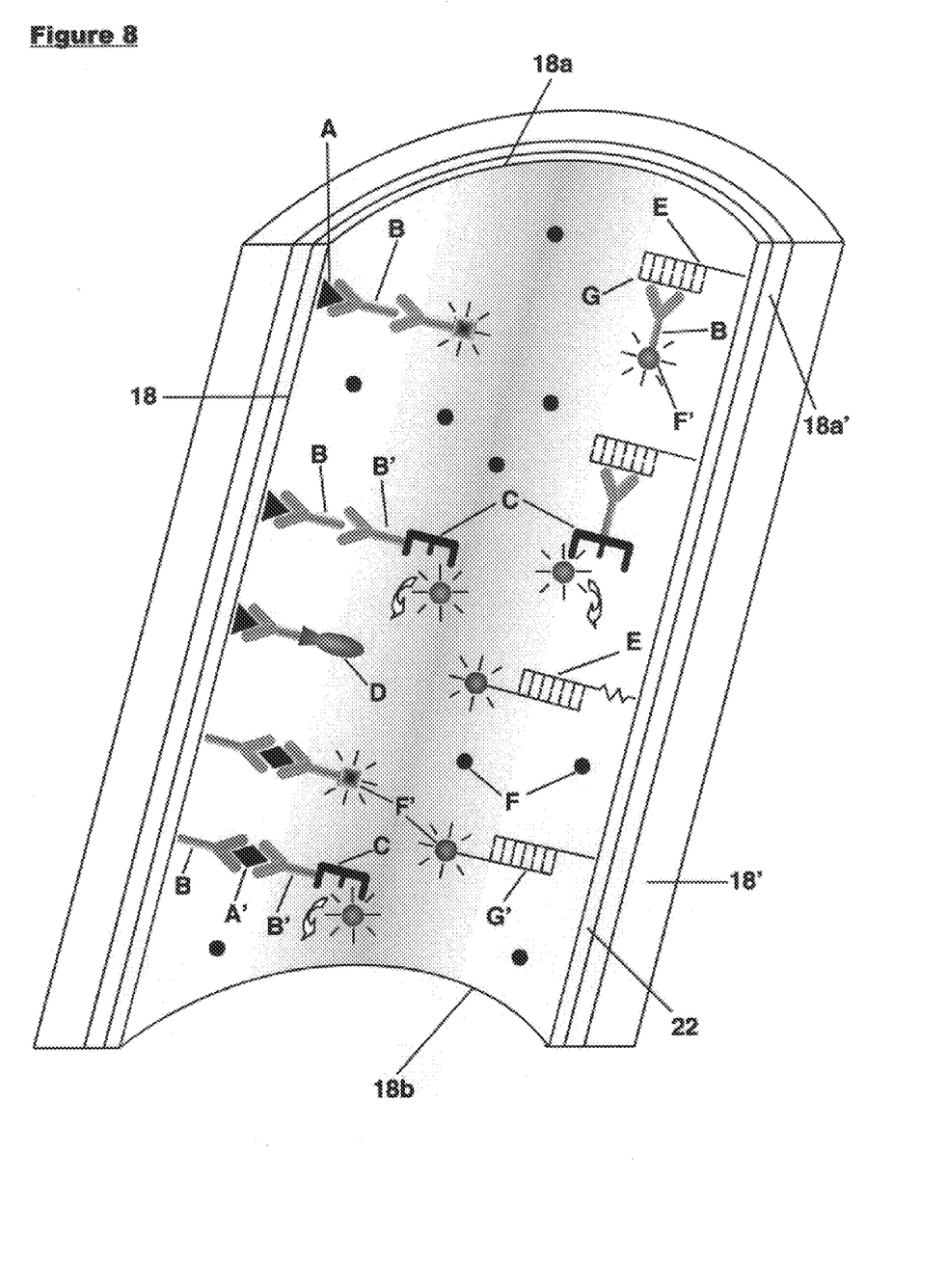
FIG. 8 is a still larger scale sectional view of the slanted channel of FIG. 7, suggesting how the various bio-molecules and proteins adhere to the inside wall of this slanted micro-channel tube of glass plate chip.

FIG. 8 schematically suggests how the biomolecules in the sample solution are bound to the inner wall of the cylindroid channel tube 18. Also in FIG. 8, element 18*a*' is an interface which has a lower refractive index than element 18. This layer could also be made of reflective metallic coating, such as aluminum or silver for the type of channels with inner metallic coating. These biomolecules may include:

antigens A, connecting antibodies B to the wall of channel tube 18;

enzymes C, conjugated with specific antibodies B' to the antigens A' and antibodies B combination;

gold particles D, also conjugated with specific antibody B;

DNA molecules E, connecting fluorescein molecules in their excited fluorescent state, F', to the inner wall of channel tube 18, or connecting a secondary antibody B being conjugated with a specific enzyme to the inner wall of channel tube 18.

Substrate F is required for colour formation of enzyme C conjugated antibody B'.

It is noted that the issues of critical angle and preferred angle is relevant to the transparent chip embodiment, but not to the chip with reflecting metallic inner coating of the micro-channels. In the latter chip embodimen, once the light enters the micro-channels, it does not have a chance to escape because of metallic coating. The transparent chip is envisioned for use with fluorescent dyes, whereas the metallic coated microchannel chip is envisioned for use mainly for non fluorescent material such as use of particles or gold in detection. The general concept of the metallic coated microchannel chip is that this reflecting inner coating on the inner wall of channels, once a particle or gold tagged biomolecule is used for detection, it become tarnished so that there appears an opaque or black layer on this reflecting coating surface and light can not pass through efficiently therefore, the reduction in light intensity reflection within the channel will determine the property of the biomolecule; it is also a cheaper and easier to implement technique. In the transparent chip concept on the other end, the fluorescent dye produces when excited more light and alerts that there is a positive result.

I claim:

1. A rigid panel chip for supporting biological samples for observation with a microscope, said rigid panel chip comprising a rigid panel defining a top flat surface, a bottom bearing surface, and at least a few channels extending generally parallel to each other from said top to bottom surfaces, each of said channels defining a top access mouth for ingress of said biological samples, wherein each of said channel is obliquely inclined so as to make an acute angle relative to an axis perpendicular to said top flat surface, and each said channel having such an inner diameter as to accommodate flow through viscosity of a biological sample containing fluid.

2. A panel chip as in claim 1, wherein said channels are cylindroid and disposed in an array selected from the group consisting of circular and conical arrays.

3. A panel chip as in claim 2, wherein said cylindroid channels have a constant diameter ranging between 10 to 500 micrometers.

4. A panel chip as in claim 3, wherein said channels diameter range between 50 to 200 micrometers.

5. A panel chip as in claim 4, wherein said channels diameter is of about 100 micrometers.

6. A panel chip as in claim 3, wherein said acute angle ranges between 30 to 60 degrees.

7. A panel chip as in claim 6, wherein said acute angle is of approximately 42 degrees.

8. A panel chip as in claim 4, wherein said acute angle ranges between 30 to 60 degrees.

9. A panel chip as in claim 8, wherein said acute angle is of approximately 42 degrees.

10. A panel chip as in claim 4, wherein the number of said channels is about two to tens of thousands, extending through the thickness of said rigid panel.

11. A panel chip as in claim 3, made from a material selected from the group consisting of: glass, quartz, polypropylene, polyolefin, nylon, and fused silica.

12. A panel chip as in claim 11, wherein said panel chip is made of transparent glass.

13. A glass panel as in claim 12, having a thickness ranging between about 0.5 to 5 millimeters.

14. A panel chip as defined in claim 1,
wherein each of said channels is lined with an inner coating made from a light reflecting metallic material.

15. A panel chip as defined in claim 14,
wherein said channel inner coating material is a metallic material selected from the group comprising aluminum and silver.

16. A panel chip as defined in claim 15, wherein said channel has a deposit of protective monolayer made from a material selected from the group consisting of silicon or magnesium fluoride.

17. A method of observation by flat surface laser scanner of biological samples in a glass panel, the glass panel of the type defining a top flat surface, a bottom bearing surface, and a plurality of channels extending generally parallel to each other from said top to bottom surfaces and each defining a top access mouth for the biological sample, the method including the following steps:
   a) Inclining the channels in an oblique fashion so as to make a significant acute angle relative to an axis perpendicular to the top flat surface of the glass panel,
   b) Enlarging the inner diameter of each said channel enough as to accommodate power assisted flow through viscosity of a biological sample containing fluid;
   c) Providing fluorescein dyes inside the biological sample containing fluid;
   d) Directing a coherent laser beam transversely through a selected channel top access mouth and coaxially into the corresponding channel, so as to excite the fluorescein dyes, wherein an optically apparent glow is generated by the excited dyes without a halo being generated about the top access mouth;
   e) Allowing sufficient time for the fluorescein dyes to project the optically apparent glow upwardly beyond said channel top access mouth; and
   f) Performing optical measurements of this upward out of channel projecting fluorescein glow to generate evidence data on the chemical properties and location of the biological samples.

18. A method as defined in claim 17, wherein said power assisted flow through of biological sample, is selected from the group consisting of low vacuum assist, and centrifugal force.

19. A method of observation by flat surface laser scanner of biological samples in a glass panel, the glass panel of the type defining a top flat surface, a bottom bearing surface, and a plurality of channels extending generally parallel to each other from said top to bottom surfaces and each defining a top access mouth for the biological sample, the method including the following steps:
   a) Inclining the channels in an oblique fashion so as to make a significant acute angle relative to an axis perpendicular to the top flat surface of the glass panel,
   b) Enlarging the inner diameter of each said channel enough as to accommodate power assisted flow through viscosity of a biological sample containing fluid;
   c) Directing a coherent laser beam transversely through a selected channel top access mouth and coaxially into the corresponding channel;
   d) Measuring deterioration of light intensity upon the binding of biomolecules to the channels inner wall; and
   e) Performing analysis of this light intensity deterioration to generate evidence data on the chemical properties and location of the biological samples.

20. A method of observation as in claim 19,
for further including a step (c1) intervening between said steps c) and d), wherein said step (c1) reads as follows:
   c1) Measuring deterioration of light intensity upon the binding of tagged gold particles to the channels.

* * * * *